United States Patent
Kobayashi

(10) Patent No.: US 12,268,768 B2
(45) Date of Patent: Apr. 8, 2025

(54) DETERGENT COMPOSITIONS

(71) Applicant: Ajinomoto Co., Inc., Tokyo (JP)

(72) Inventor: Shun Kobayashi, Kawasaki (JP)

(73) Assignee: Ajinomoto Co. Inc., Tokyo (JP)

( * ) Notice: Subject to any disclaimer, the term of this patent is extended or adjusted under 35 U.S.C. 154(b) by 0 days.

(21) Appl. No.: 16/862,059

(22) Filed: Apr. 29, 2020

(65) Prior Publication Data

US 2020/0253849 A1 Aug. 13, 2020

Related U.S. Application Data

(63) Continuation of application No. PCT/JP2018/040814, filed on Nov. 2, 2018.

(30) Foreign Application Priority Data

Nov. 6, 2017 (JP) ................. 2017-213936

(51) Int. Cl.
*A61K 8/44* (2006.01)
*A61Q 5/02* (2006.01)
*A61Q 19/10* (2006.01)

(52) U.S. Cl.
CPC .......... *A61K 8/44* (2013.01); *A61Q 5/02* (2013.01); *A61Q 19/10* (2013.01); A61K 2800/596 (2013.01)

(58) Field of Classification Search
None
See application file for complete search history.

(56) References Cited

U.S. PATENT DOCUMENTS

| 6,582,687 | B1 | * | 6/2003 | Hamano | A61K 8/86 424/78.03 |
|---|---|---|---|---|---|
| 8,338,483 | B2 | | 12/2012 | Klug et al. | |
| 9,662,287 | B2 | | 5/2017 | Klug et al. | |
| 2017/0218305 | A1 | | 8/2017 | Yumioka | |
| 2017/0226048 | A1 | | 8/2017 | Klug et al. | |
| 2017/0281497 | A1 | | 10/2017 | Kobayashi et al. | |
| 2017/0283741 | A1 | | 10/2017 | Behler et al. | |

FOREIGN PATENT DOCUMENTS

| CN | 101688151 | * | 4/2016 | |
|---|---|---|---|---|
| EP | 1428519 | A2 * | 6/2004 | ............... A61K 8/34 |
| EP | 1 586 625 | A1 | 10/2005 | |
| JP | 59-230099 | | 12/1984 | |
| JP | 61-271398 | | 12/1986 | |
| JP | H 6-57289 | | 3/1994 | |
| JP | 6-128121 | | 5/1994 | |
| JP | 06-158089 | A | 6/1994 | |
| JP | H 11-189788 | | 7/1999 | |
| JP | 2001-026795 | | 1/2001 | |
| JP | 2003-034670 | | 2/2003 | |
| JP | 2003-201213 | A | 7/2003 | |
| JP | 2004-155716 | A | 6/2004 | |
| JP | 2005-325204 | A | 11/2005 | |
| JP | 2008-127492 | | 6/2008 | |
| JP | 2009-051945 | | 3/2009 | |
| JP | 2013-166739 | A | 8/2013 | |
| JP | 5496905 | | 5/2014 | |
| JP | 2014-523434 | | 9/2014 | |
| JP | 2015221762 | * | 12/2015 | |
| WO | WO-03039496 | A1 * | 5/2003 | ............... A61K 8/44 |
| WO | WO 2004/061060 | A1 | 7/2004 | |
| WO | WO 2016/080207 | A1 | 4/2016 | |
| WO | WO 2016/104692 | A1 | 6/2016 | |

OTHER PUBLICATIONS

JP 2015221762, Dec. 2015, Sakamoto et al., English Translation.*
International Search Report in PCT/JP2018/040814 issued Jan. 29, 2019.
Extended European Search Report issued Jul. 20, 2021 in corresponding European Patent Application No. 18872237.5, 9 pages.
Margaret Harris et al., "The Impact of Virgin Coconut Oil and High-Oleic Safflower Oil on Body Composition, Lipids, and Inflammatory Markers in Postmenopausal Women", Journal Of Medicinal Food, vol. 20, No. 4, 2017, pp. 345-351.
Office Action issued on Sep. 6, 2022, in the corresponding Japanese Patent Application No. 2019-550495 (with English machine translation).
Japanese Office Action issued Jan. 24, 2023 in Japanese Patent Application No. 2019-550495 (with unedited computer-generated English Translation), 6 pages.
European Office Action issued Jul. 30. 2024 in European Patent Application No. 18 872 237.5, 6 pages.

(Continued)

*Primary Examiner* — David J Blanchard
*Assistant Examiner* — Sarah J Chickos
(74) *Attorney, Agent, or Firm* — Oblon, McClelland, Maier & Neustadt, L.L.P.

(57) ABSTRACT

The present invention provides a detergent composition containing N-acyl acidic amino acids that, even at low pH, exhibits excellent solubility, has good storage stability, and creates a quality foam with satisfactory lathering performance. Specifically, the present invention provides a detergent composition and the like comprising:

(A) an N-unsaturated acyl acidic amino acid wherein the unsaturated acyl is a linear acyl with 8 to 20 carbon atoms;

(B) an N-saturated acyl acidic amino acid wherein the saturated acyl is a linear acyl with 8 to 14 carbon atoms; and (C) optionally, an N-saturated acyl acidic amino acid wherein the saturated acyl is a linear acyl with 16 to 20 carbon atoms;

wherein the weight ratio of the component (A) to the component (B) (A/B) is 0.01 to 0.80, and the weight ratio of the component (C) to the component (B) (C/B) is 0.00 to 0.32.

15 Claims, No Drawings

(56) References Cited

OTHER PUBLICATIONS

Anonymous., "Final Report on the Safety Assessment of Coconut Oil, Coconut Acid, Hydrogenated Coconut Acid, and Hydrogenated Coconut Oil," Journal of the American College of Toxicology, vol. 5, No. 3, 1986, pp. 103-121, XP093189120.
Japanese Office Action dated Sep. 10, 2024 in corresponding Japanese Application No. 2023-136235 (with English Machine Translation).
Office Action dated Feb. 12, 2025, in corresponding JP Patent Appl. No. 2023-136235 (with English Machine translation).

* cited by examiner

DETERGENT COMPOSITIONS

TECHNICAL FIELD

The present invention relates to detergent compositions.

BACKGROUND ART

Anionic surfactants such as alkyl sulfate ester salts, polyoxyethylene alkyl ether sulfate salts and alkylbenzene sulfonate salts have high solubility and good lathering performance in a weakly acidic region (similar to the skin's pH), and thus have gained wide use as surfactants added to liquid detergents such as face washes, body washes and hair shampoos. On the other hand, these anionic surfactants have defects in that they in the form of a foam are not quickly rinsed away and they are irritating to the skin.

Under such circumstances, N-acyl acidic amino acids that are carboxylic anionic surfactants are used as mild and safe detergents offering a good feel after use (Patent Literature 1). However, N-acyl acidic amino acids have problems in that they form large bubbles and tend to be incapable of achieving creaminess of a foam, and in that they are easily precipitated at low pH because they are carboxylic anionic surfactants.

Studies have been reported in which an N-acyl glutamic acid that is a type of N-acyl acidic amino acids is formulated with a controlled fatty acid composition so as to enhance the function of the N-acyl glutamic acid (Patent Literatures 2 and 3). However, these reports on detergent in the form of powder, granules or cream. No studies have been reported on the improvements in the stability and lathering performance of liquid detergent. Thus, there have been demands for the development of liquid detergent that, even at low pH, are free from precipitation and of stable quality and lather well.

PRIOR ART DOCUMENTS

Patent Literatures

Patent Literature 1: Japanese Patent Application Laid-open No. H6-158089
Patent Literature 2: Japanese Patent Application Laid-open No. 2009-51945
Patent Literature 3: Japanese Patent Application Laid-open No. 2003-34670

SUMMARY OF INVENTION

Problem to be Solved by the Invention

The object of the present invention is to provide a detergent composition containing N-acyl acidic amino acids that, even at low pH, exhibits excellent solubility, has good storage stability, and creates a quality foam with satisfactory lathering performance.

Means for Solving Problem

As a result of extensive studies, the present inventors have found that a detergent composition that comprises:
 (A) an N-unsaturated acyl acidic amino acid wherein the unsaturated acyl is a linear acyl with 8 to 20 carbon atoms;
 (B) an N-saturated acyl acidic amino acid wherein the saturated acyl is a linear acyl with 8 to 14 carbon atoms; and
 (C) optionally, an N-saturated acyl acidic amino acid wherein the saturated acyl is a linear acyl with 16 to 20 carbon atoms;
and that has a higher content of the component (B) than the content of the component (C) advantageously exhibits excellent solubility and is not precipitated even at a low pH (i.e., an acidic pH), thus contributing to storage stability, and also creates a thick and elastic foam, that is, has excellent lathering performance and offers a superior foam quality. Formulating the detergent composition so as to have a low pH advantageously suppresses the growth of bacteria and thus enhances storage stability, and is also advantageous in that such a pH level similar to the skin's pH leads to good applicability on the skin. By virtue of these advantages, among numerous uses in a wide range of fields including various industrial products and foods, the detergent composition will be particularly suited for use as cosmetics that are used frequently on daily basis according to one's tastes and need to satisfy sophisticated sensory requirements by users.

Accordingly, the present invention is as follows.

[1] A detergent composition comprising:
 (A) an N-unsaturated acyl acidic amino acid wherein the unsaturated acyl is a linear acyl with 8 to 20 carbon atoms;
 (B) an N-saturated acyl acidic amino acid wherein the saturated acyl is a linear acyl with 8 to 14 carbon atoms; and
 (C) optionally, an N-saturated acyl acidic amino acid wherein the saturated acyl is a linear acyl with 16 to 20 carbon atoms;
 wherein the weight ratio of the component (A) to the component (B) (A/B) is 0.01 to 0.80, and
 the weight ratio of the component (C) to the component (B) (C/B) is 0.00 to 0.32.

[2] The detergent composition according to [1], wherein the component (A) is an N-unsaturated acyl acidic amino acid wherein the unsaturated acyl is a linear acyl with 16 to 20 carbon atoms.

[3] The detergent composition according to [2], wherein the component (A) is an N-oleoyl acidic amino acid.

[4] The detergent composition according to any of [1] to [3], wherein the component (B) comprises one, or two or more selected from the group consisting of N-capryloyl acidic amino acids, N-decanoyl acidic amino acids, N-lauroyl acidic amino acids, and N-myristoyl acidic amino acids.

[5] The detergent composition according to [4], wherein the component (B) comprises an N-lauroyl acidic amino acid and/or an N-myristoyl acidic amino acid.

[6] The detergent composition according to any one of [1] to [5], wherein the component (C) comprises an N-palmitoyl acidic amino acid and/or an N-stearoyl acidic amino acid.

[7] The detergent composition according to any of [1] to [6], wherein the N-unsaturated acyl acidic amino acid is an N-unsaturated acyl glutamic acid, and the N-saturated acyl acidic amino acids are N-saturated acyl glutamic acids.

[8] The detergent composition according to any of [1] to [7], wherein the weight ratio of the component (A) to the component (B) (A/B) is 0.02 to 0.60.

[9] The detergent composition according to any of [1] to [8], wherein the weight ratio of the component (C) to the component (B) (C/B) is 0.01 to 0.30.

[10] The detergent composition according to any of [1] to [9], wherein the pH is 4.0 to 7.0.
[11] The detergent composition according to [10], wherein the pH is 4.5 to 7.0.
[12] A cosmetic comprising the detergent composition according to any of [1] to [11].
[13] The cosmetic according to [12], wherein the pH is 4.5 to 7.0.

Effect of the Invention

The detergent composition of the present invention, even at low pH, exhibits excellent solubility, has good storage stability, and creates a quality foam with satisfactory lathering performance. The detergent composition of the present invention has good applicability on the skin and is particularly suited for use as a cosmetic.

EMBODIMENTS FOR CARRYING OUT THE INVENTION

The present invention provides a detergent composition that includes:
(A) an N-unsaturated acyl acidic amino acid wherein the unsaturated acyl is a linear acyl with 8 to 20 carbon atoms;
(B) an N-saturated acyl acidic amino acid wherein the saturated acyl is a linear acyl with 8 to 14 carbon atoms; and
(C) optionally, an N-saturated acyl acidic amino acid wherein the saturated acyl is a linear acyl with 16 to 20 carbon atoms (hereinafter, which may be simply abbreviated as "composition").

In the description, "linear acyl with n carbon atoms" means an acyl represented by $C_{n-1}H_m$—CO— (in which a hydrogen atom may be substituted). When the acyl is a saturated acyl, $m=2n-1$. When the acyl is an unsaturated acyl, m is determined appropriately in accordance with the number of carbon atoms and the number of unsaturation.

In the description, "N-acyl acidic amino acid wherein the acyl is a linear acyl with n carbon atoms" means a compound represented by $C_{n-1}H_m$—CO—NH—CHR—COOH (in which hydrogen atoms denoted by $H_m$ may be substituted, m is as defined above, and R denotes a side chain of the acidic amino acid) if expressed as a free form. That is, "N-acyl acidic amino acid" means a compound resulting from the substitution of an acidic amino acid with an acyl in place of one hydrogen atom on the amino group. "N-saturated acyl acidic amino acid" means an N-acyl acidic amino acid in which the acyl is a saturated acyl. "N-unsaturated acyl acidic amino acid" means an N-acyl acidic amino acid in which the acyl is an unsaturated acyl. "N-acyl acidic amino acid" may be a free form of an N-acyl acidic amino acid or may be a salt of an N-acyl acidic amino acid.

Examples of the salts of N-acyl acidic amino acids include inorganic salts and organic salts. Examples of the inorganic salts include salts with metals (e.g., monovalent metals such as lithium, sodium, potassium, rubidium and cesium, and divalent metals such as calcium, magnesium and zinc), and salts with inorganic bases (e.g., ammonia). Examples of the organic salts include salts with organic bases (e.g., ethylenediamine, propylenediamine, ethanolamine, monoalkylethanolamine, dialkylethanolamine, diethanolamine, triethanolamine, lysine, arginine, histidine and ornithine).

In the description, for the purpose of convenience, an N-acyl acidic amino acid is sometimes described as being derived from a fatty acid represented by $C_{n-1}H_m$—COOH or a derivative thereof. Further, in the description, "linear acyl with n carbon atoms" and a fatty acid or the like from which the acyl is derived are sometimes written as "Cn". For example, "lauroyl acidic amino acid (C12)" means a compound resulting from the substitution of an acidic amino acid with a lauroyl group that is an acyl group derived from lauric acid (C12), in place of one hydrogen atom on the amino group ($C_{11}H_{23}$CO—NH—CHR—COOH wherein R denotes a side chain of the acidic amino acid). When an N-acyl acidic amino acid is obtained from a fatty acid, the N-acyl acidic amino acid may be obtained by, for example, reacting a fatty acid derivative represented by $C_{n-1}H_m$—COX (X is any monovalent group such as a halogen atom selected from the group consisting of fluorine, chlorine, bromine and iodine) with a salt of an acidic amino acid (the salt may be, for example, any of the aforementioned inorganic salts and organic salts).

Examples of the N-unsaturated acyl acidic amino acids as the components (A) include N-monounsaturated acyl acidic amino acids, N-diunsaturated acyl acidic amino acids, N-triunsaturated acyl acidic amino acids, N-tetraunsaturated acyl acidic amino acids and N-pentaunsaturated acyl acidic amino acids. The unsaturated acyls in the N-unsaturated acyl acidic amino acids are linear acyls having 8 to 20 carbon atoms, preferably 16 to 20 carbon atoms.

Examples of the monounsaturated fatty acids from which the N-monounsaturated acyl acidic amino acids are derived include myristoleic acid (C14), palmitoleic acid (C16), oleic acid (C18), elaidic acid (C18), vaccenic acid (C18), gadoleic acid (C20) and eicosenoic acid (C20).

Examples of the diunsaturated fatty acids from which the N-diunsaturated acyl acidic amino acids are derived include linoleic acid (C18) and eicosadienoic acid (C20).

Examples of the triunsaturated fatty acids from which the N-triunsaturated acyl acidic amino acids are derived include α-linolenic acid (C18), γ-linolenic acid (C18) and pinolenic acid (C18).

Examples of the tetraunsaturated fatty acids from which the N-tetraunsaturated acyl acidic amino acids are derived include stearidonic acid (C18), arachidonic acid (C20) and eicosatetraenoic acid (C20).

Examples of the pentaunsaturated fatty acids from which the N-pentaunsaturated acyl acidic amino acids are derived include bosseopentaenoic acid (C18) and eicosapentaenoic acid (C20).

The N-unsaturated acyl acidic amino acid as the component (A) is most preferably an N-oleoyl acidic amino acid.

Examples of the N-saturated acyl acidic amino acids wherein the saturated acyl is a linear acyl with 8 to 14 carbon atoms as the components (B) include capryloyl acidic amino acids (C8), decanoyl acidic amino acids (C10), lauroyl acidic amino acids (C12) and myristoyl acidic amino acids (C14). The component (B) may be a single N-saturated acyl acidic amino acid, or may include two or more kinds of N-saturated acyl acidic amino acids. Specifically, the component (B) may include one, or two or more selected from the group consisting of N-capryloyl acidic amino acids, N-decanoyl acidic amino acids, N-lauroyl acidic amino acids, and N-myristoyl acidic amino acids. The component (B) preferably includes an N-lauroyl acidic amino acid and/or an N-myristoyl acidic amino acid. The total content of an N-lauroyl acidic amino acid and an N-myristoyl acidic amino acid in the components (B) may be, for example, not less than 50 wt %, preferably not less than 60 wt %, more preferably not less than 70 wt %, still more preferably not less than 75 wt %, further preferably not less than 80 wt %, and particularly preferably not less than 85 wt %. More specifically, the total content of an N-lauroyl acidic amino acid and an N-myristoyl acidic amino acid in the components (B) may be, for example, 50 to 100 wt %, preferably 60 to 100 wt %, more preferably 70 to 100 wt %, still more preferably 75 to 100 wt %, further preferably 80 to 100 wt %, and particularly preferably 85 to 100 wt %.

Examples of the N-saturated acyl acidic amino acids wherein the saturated acyl is a linear acyl with 16 to 20 carbon atoms as the components (C) include palmitoyl acidic amino acids (C16) and stearoyl acidic amino acids (C18). The component (C) may be a single N-saturated acyl acidic amino acid, or may include two or more kinds of N-saturated acyl acidic amino acids. Specifically, the component (C) may include an N-palmitoyl acidic amino acid and/or an N-stearoyl acidic amino acid.

The "acidic amino acid" in the "N-acyl acidic amino acid" is an amino acid having an acidic side chain. Examples of the acidic amino acids include glutamic acid and asparaginic acid.

From points of view such as enhancements in solubility of the component (A) at low pH, the weight ratio of the component (A) to the component (B) (A/B) is not less than 0.01, and may be preferably not less than 0.02, more preferably not less than 0.03, and still more preferably not less than 0.04. From points of view such as reducing the decrease in lathering performance due to a high content of the component (A), and contributions to quick lathering and solution stability by virtue of the component (B) contained in a high content, the weight ratio of the component (A) to the component (B) (A/B) is not more than 0.80, and may be preferably not more than 0.60, more preferably not more than 0.40, and still more preferably not more than 0.35. More specifically, the weight ratio of the component (A) to the component (B) (A/B) is 0.01 to 0.80, and may be preferably 0.02 to 0.60, more preferably 0.03 to 0.40, and still more preferably 0.04 to 0.35. Alternatively, from the point of view of further enhancements in foam volume, the weight ratio of the component (A) to the component (B) (A/B) may be preferably not less than 0.05, more preferably not less than 0.06, still more preferably not less than 0.07, and particularly preferably not less than 0.08. From the point of view of further enhancements in foam volume, the weight ratio of the component (A) to the component (B) (A/B) may be preferably not more than 0.30, more preferably not more than 0.25, still more preferably not more than 0.20, and particularly preferably not more than 0.15. From the point of view of further enhancements in foam volume, the weight ratio of the component (A) to the component (B) (A/B) may be preferably 0.05 to 0.30, more preferably 0.06 to 0.25, still more preferably 0.07 to 0.20, and particularly preferably 0.08 to 0.15.

The weight ratio of the component (C) to the component (B) (C/B) may be 0.00 or above. When the weight ratio of the component (C) to the component (B) (C/B) is 0.00, the component (C) is absent. From points of view such as contributions of the component (C) to enhancing the foam quality (density), the weight ratio may be preferably not less than 0.01, more preferably not less than 0.02, still more preferably not less than 0.04, and particularly preferably not less than 0.05. From points of view such as decrease in stability which is caused by precipitation due to a high content of the component (C), and contributions to quick lathering and solution stability by virtue of the component (B) contained in a high content, the weight ratio of the component (C) to the component (B) (C/B) is not more than 0.32, and may be preferably not more than 0.30, more preferably not more than 0.27, still more preferably not more than 0.24, and particularly preferably not more than 0.21. More specifically, the weight ratio of the component (C) to the component (B) (C/B) is 0.00 to 0.32, and may be preferably 0.01 to 0.30, more preferably 0.02 to 0.27, still more preferably 0.04 to 0.24, and particularly preferably 0.05 to 0.21. Alternatively, from points of view such as simple preparation of the detergent composition of the present invention using less components, the weight ratio of the component (C) to the component (B) (C/B) is 0.00 to 0.32, and may be preferably 0.00 to 0.30, more preferably 0.00 to 0.27, still more preferably 0.00 to 0.24, and particularly preferably 0.00 to 0.21.

The detergent composition of the present invention may include the components (A), (B), and/or (C) in a water-soluble medium. The water-soluble medium may be any water-soluble solvent. Examples of the water-soluble media include aqueous solutions. The aqueous solutions may have or may not have a buffering capacity. Examples of the aqueous solutions include waters (e.g., distilled water, sterilized distilled water, purified water, saline), phosphate buffer, tris-hydrochloride buffer, TE (tris-EDTA) buffer, carbonate buffer, borate buffer, tartrate buffer, glycine buffers, citrate buffer and acetate buffer.

The content of the component (A) is not particularly limited and is variable depending on various conditions such as the types and concentrations of other components contained in the composition of the present invention, and the pH. From points of view such as enhancements in solubility at low pH, the content may be, for example, not less than 1 wt %, preferably not less than 2 wt %, and more preferably not less than 3%. From points of view such as the fact that the lathering performance is lowered if the content of the component (A) is too high, the content may be, for example, not more than 25 wt %, preferably not more than 23 wt %, and more preferably not more than 22 wt %. More specifically, the content of the component (A) may be, for example, 1 to 25 wt %, preferably 2 to 23 wt %, and more preferably 3 to 22 wt %.

The content of the component (B) is not particularly limited and is variable depending on various conditions such as the types and concentrations of other components contained in the composition of the present invention, and the pH. From points of view such as contributions to quick lathering and solution stability, the content may be, for example, not less than 60 wt %, preferably not less than 65 wt %, and more preferably not less than 70%. The content of the component (B) may be, for example, not more than 99 wt %, preferably not more than 97 wt %, and more preferably not more than 95 wt %. More specifically, the content of the component (B) may be, for example, 60 to 99 wt %, preferably 65 to 97 wt %, and more preferably 70 to 95 wt %.

The content of the component (C) is not particularly limited and is variable depending on various conditions such as the types and concentrations of other components contained in the composition of the present invention, and the pH. The content may be 0 wt % or above. When the content of the component (C) is 0 wt %, the component (C) is absent. From points of view such as contributions to enhancements in foam quality (density), the content may be, for example, not less than 0.1 wt %, preferably not less than 1 wt %, and more preferably not less than 5%. From points of view such as the fact that a high content of the component (C) results in precipitation and a consequent decrease in stability, the content may be, for example, not more than 20 wt %, preferably not more than 18 wt %, and more preferably not more than 16 wt %. More specifically, the content of the component (C) may be, for example, 0 to 20 wt %, preferably 1 to 18 wt %, and more preferably 5 to 16 wt %.

The composition of the present invention is preferably weakly acidic from the points of view of storage stability by suppression of bacterial growth (antiseptic action), and low irritation to skin by virtue of the pH similar to skin's pH (weakly acidic). The pH of the composition of the present invention may be, for example, 4.0 to 7.0, and, from the point of view of bringing the pH close to the skin's pH, may be preferably 4.5 to 7.0, and more preferably 4.8 to 6.5. The composition of the present invention shows excellent solubility and is prevented from precipitation even at low pH, and this fact adds further storage stability. Further, while anionic surfactants in general tend to show low lathering performance at low pH, the composition of the present invention lathers well even at low pH. The pH may be controlled with a pH adjuster. Examples of the pH adjusters include the aforementioned aqueous solutions (buffer), acidic substances (e.g., hydrochloric acid, sulfuric acid, nitric acid, citric acid), and alkaline substances (e.g., hydroxides of alkali metals such as sodium and potassium, and of alkaline earth metals such as calcium).

The composition of the present invention may further include other components such as additional detergent components, polyhydric alcohols, thickeners, stabilizers, preservatives, flavours and colorants. The specific types and amounts of these components may be selected appropriately.

Examples of the additional detergent components include surfactants such as anionic surfactants, amphoteric surfactants and nonionic surfactants, and micro solids (e.g., microspheres, scrub particles).

The anionic surfactants contain one, or two or more kinds of anionic groups. Examples of the anionic groups include carboxyl groups, sulfonate groups, sulfate groups and phosphate groups. Examples of the anionic surfactants include higher fatty acids, N-acyl amino acids, N-acyl taurines, alkyl ether carboxylic acids, alkyl phosphoric acids, polyoxyethylene alkyl ether phosphoric acids, alkyl sulfuric acids, polyoxyethylene alkyl ether sulfuric acids, alkyl chain-containing sulfonic acid compounds, and salts thereof.

The amphoteric surfactants contain one, or two or more kinds of the anionic groups described above, and one, or two or more kinds of cationic groups. Examples of the cationic groups include ammonium groups, primary amino groups, secondary amino groups, tertiary amino groups and quaternary amino groups. Examples of the amphoteric surfactants include amidobetaine-type amphoteric surfactants, acetic acid betaine-type amphoteric surfactants, sulfobetaine-type amphoteric surfactants and imidazoline-type amphoteric surfactants (e.g., lauroamphoacetic acid and salts thereof).

Examples of the nonionic surfactants include alkyl polyglucosides formed by glycoside bonding of sugars and higher alcohols.

Examples of the polyhydric alcohols include dihydric alcohols (e.g., ethylene glycol, propylene glycol, 1,3-propanediol, 1,2-butylene glycol, 1,3-butylene glycol, 2,3-butylene glycol, 1,4-butanediol, 2-butene-1,4-diol, 1,5-pentanediol, 1,2-pentanediol, isoprene glycol, hexylene glycol, diethylene glycol, dipropylene glycol, monoglyceride (monoacylglycerol)), trihydric alcohols (e.g., glycerol, trimethylolpropane, 1,2,6-hexanetriol), tetrahydric alcohols (e.g., diglycerol, pentaerythritol), higher valence alcohols, and salts thereof (e.g., the inorganic salts and the organic salts described above). Examples of the higher valance alcohols include optionally substituted sugar alcohols (e.g., monosaccharide alcohols such as sorbitol, mannitol, sucrose, glucose and mannose, disaccharide alcohols such as trehalose, and polysaccharide alcohols such as hyaluronic acid and xanthan gum), polymers of the aforementioned dihydric to tetrahydric alcohols (e.g., polyglycol, polyglycerol), and salts thereof (e.g., the inorganic salts and the organic salts described above). The polyhydric alcohols may be preferably dihydric to tetrahydric alcohols, and more preferably dihydric or trihydric alcohols.

Examples of the thickeners include carrageenan, dextrin, methylcellulose, ethylcellulose, hydroxyethylcellulose, hydroxypropylcellulose, hydroxypropylmethylcellulose, polyacrylic acid, polymethacrylic acid, carboxyvinyl polymer (Carbomer), (acrylic acid/alkyl (C10-30) acrylate) copolymers, and xanthan gum.

Examples of the stabilizers include ascorbic acid, sodium pyrosulfite and EDTA.

Examples of the preservatives include ethyl paraoxybenzoate, sodium benzoate, salicylic acid, sorbic acid, parabens (such as methylparaben and propylparaben), and sodium hydrogen sulfite.

Examples of the flavours include natural flavours and synthetic flavours. Examples of the natural flavours include rose oil, jasmine oil, neroli oil, lavender oil, ylang ylang oil, tuberose oil, clary sage oil, clove oil, peppermint oil, geranium oil, patchouli oil, sandalwood oil, cinnamon oil, coriander oil, nutmeg oil, pepper oil, lemon oil, orange oil, bergamot oil, opoponax oil, vetiver oil, orris oil and oakmoss oil. Examples of the synthetic flavours include limonene (orange), β-caryophyllene (woody), cis-3-hexenol (fresh green young leaves), linalool (lily of the valley), farnesol (fresh green note floral), β-phenylethyl alcohol (rose), 2,6-nonadienal (violet, cucumber), citral (lemon), α-hexylcinnamic aldehyde (jasmine), β-ionone (violet when diluted), ι-carvone (spearmint), cyclopentadecanone (musk), linalyl acetate (bergamot, lavender), benzyl benzoate (balsam), γ-undecalactone (peach), eugenol (clove), rose oxide (green floral), indole (jasmine when diluted), phenylacetaldehyde dimethyl acetal (hyacinth), aurantiol (orange flower) and menthol (peppermint) (the odors are described in the parentheses).

Examples of the colorants include organic pigments (e.g., red pigments such as Red No. 201, blue pigments such as Blue No. 404, orange pigments such as Orange No. 203, yellow pigments such as Yellow No. 205, green pigments such as Green No. 3, organic lake pigments such as zirconium lake, natural colorants such as chlorophyll), and inorganic pigments (e.g., white pigments such as titanium oxide, color pigments such as iron oxide, extender pigments such as talc, pearl pigments such as mica).

The composition of the present invention may be provided in various forms such as, for example, liquids, gels, pastes, creams and foams.

The composition of the present invention may be formulated according to a common procedure into, for example, any form of cosmetic that is applicable to skin, hair, scalp, etc. The cosmetic of the present invention may be, for example, a detergent for animals such as humans, and is suited for use in applications such as body shampoos, hand soaps, facial washes, cleansing lotions, cleansing creams, massage creams and hair shampoos. Preferred characteristics (e.g., pH) of the cosmetic of the present invention are similar to the preferred characteristics of the composition of the present invention described above.

EXAMPLES

The present invention will be described in greater detail by presenting Examples hereinbelow. However, it should be construed that the scope of the present invention is not limited to such Examples.

Production Example of N-Acyl Glutamic Acid

An acid chloride of a mixture of fatty acids with specific proportions was reacted with a reaction amount of a glutamate salt sufficiently under basic conditions. After the completion of the reaction, an acid was added to precipitate a crystal, which was then subjected to filtration and drying steps. As a result, an N-acyl glutamic acid powder was obtained. Incidentally, HPLC of the N-acyl glutamic acids obtained showed that the reaction had proceeded sufficiently.

Method for Preparing Compositions of Examples 1 to 5 and Comparative Examples 1 to 4

N-Acyl glutamic acids obtained as described in Production Example using an acid chloride of a composition of fatty acids described in Table 1 were neutralized with an aqueous sodium hydroxide solution to give an aqueous solution of sodium N-acyl glutamates. The aqueous solution obtained was controlled to pH 4.5 and 10 wt % concentration. A detergent composition was thus obtained. The detergent composition obtained was tested. The results are described in Table 1.

Method for Preparing Compositions of Example 6 and Comparative Example 5

N-Acyl glutamic acids that had been obtained as described in Production Example from the acid chloride of a composition of fatty acids used in Example 1 or Comparative Example 1 were neutralized with an aqueous sodium hydroxide solution to give a 25% aqueous solution of sodium N-acyl glutamates. The raw materials described in Table 2 that included these sodium N-acyl glutamates were mixed together by stirring at 80° C., gradually cooled to room temperature, and adjusted to pH 5.0. A detergent composition was thus obtained. The detergent composition obtained was loaded into a pump foamer bottle and was tested. The results are described in Table 2.

Evaluation of Storage Stability

The liquid detergent compositions prepared as described above were loaded into 50 ml vial bottles and were allowed to stand at room temperature for one week. Thereafter, the liquid detergent compositions were visually inspected for the presence or absence of precipitates and were evaluated based on the following criteria.
A: Transparent liquid
B: Whitish liquid Evaluation of Foam Volume Exactly 2 g of the liquid detergent composition prepared was added to a 500 ml beaker and was diluted to 100 g with 35° C. warm water. Thereafter, the composition was caused to lather by mixing it with a commercial hand mixer for 10 seconds, and the scale on the beaker was read immediately to evaluate the foam volume under the following criteria.
  a: The foam volume was 251 mL or more.
  b: The foam volume was 225 to 250 mL.
  c: The foam volume was 201 to 225 mL.
  d: The foam volume was 200 mL or less.

Evaluation of Foam Quality

The foam dispensed from the pump foamer bottle was analyzed with a rheometer (AR-G2, TA Instruments) to measure the dynamic viscoelasticity (measurement tool: aluminum cone plate 40 mm in diameter and 2° in cone angle, measurement temperature: 35° C.). Based on the Bingham yield stress (Pa) obtained, the foam quality was evaluated based on the following criteria. (According to a report, a foam with a higher Bingham yield stress is generally more elastic and tough.)
  a: The Bingham yield stress was 10.1 Pa or above.
  b: The Bingham yield stress was 7.6 to 10.0 Pa.
  c: The Bingham yield stress was 5.1 to 7.5 Pa.
  d: The Bingham yield stress was 5.0 Pa or below.

Sensory Evaluation Test

[Evaluation Procedure]
The composition was used by ten professional evaluation panelists and was evaluated on a 5-point scale based on the following criteria in terms of foam volume, foam elasticity and moisture retention after rinsing. Further, the composition was rated based on the average of the results.

Evaluation Criteria

5 Points: Excellent
4 Points: Good
3 Points: Fair
2 Points: Poor
1 Point: Very poor Rating Criteria a: The average was 4 points or above.
b: The average was 3 points to below 4 points.
c: The average was 2 points to below 3 points.
d: The average was below 2 points.

TABLE 1

Evaluation of 10 wt % aqueous solutions of compositions of Examples 1 to 5 and Comparative Examples 1 to 4 at pH 4.5

| | Component | Examples | | | | | Comparative Examples | | | |
| --- | --- | --- | --- | --- | --- | --- | --- | --- | --- | --- |
| | | 1 | 2 | 3 | 4 | 5 | 1 | 2 | 3 | 4 |
| Proportions (wt %) | (A) Sodium N-oleoyl glutamate (C18F1) | 9 | 7 | 22 | 4 | 5 | 0 | 9 | 41 | 19 |

TABLE 1-continued

Evaluation of 10 wt % aqueous solutions of compositions of
Examples 1 to 5 and Comparative Examples 1 to 4 at pH 4.5

|   | Component | Examples | | | | | Comparative Examples | | | |
|---|---|---|---|---|---|---|---|---|---|---|
|   |   | 1 | 2 | 3 | 4 | 5 | 1 | 2 | 3 | 4 |
| (B) | Sodium N-capryloyl (C8) | 5 | 0 | 4 | 5 | 0 | 5 | 2 | 3 | 0 |
|   | Sodium N-decanoyl glutamate (C10) | 5 | 1 | 4 | 6 | 0 | 6 | 3 | 3 | 0 |
|   | Sodium N-lauroyl glutamate (C12) | 56 | 56 | 47 | 59 | 95 | 62 | 51 | 32 | 40 |
|   | Sodium N-myristoyl glutamate (C14) | 20 | 20 | 17 | 21 | 0 | 22 | 12 | 12 | 2 |
| (C) | Sodium N-palmitoyl glutamate (C16) | 4 | 14 | 4 | 4 | 0 | 4 | 9 | 8 | 13 |
|   | Sodium N-stearoyl glutamate (C18) | 1 | 2 | 2 | 1 | 0 | 1 | 14 | 1 | 26 |
|   | Total | 100 | 100 | 100 | 100 | 100 | 100 | 100 | 100 | 100 |
|   | Weight ratio (A/B) | 0.10 | 0.09 | 0.31 | 0.04 | 0.05 | 0.00 | 0.13 | 0.82 | 0.45 |
|   | Weight ratio (C/B) | 0.06 | 0.21 | 0.08 | 0.05 | 0 | 0.05 | 0.34 | 0.18 | 0.93 |
| Results | Storage stability | A | A | A | A | A | B | B | B | B |
|   | Evaluation of foam volume (ml) | a 255 | a 267 | b 245 | b 250 | b 235 | d 200 | c 220 | d 130 | b 245 |
|   | Sensory evaluation (foam volume) | a | a | b | b | b | d | c | d | b |

TABLE 2

Evaluation of compositions of Example 6 and Comparative Example 5

|   |   | Example 6 | Comparative Example 5 |
|---|---|---|---|
| Proportions (wt %) | Sodium N-acyl glutamates (25% aqueous solution) obtained by reaction with proportion described in Example 1 | 30 | — |
|   | Sodium N-acyl glutamates (25% aqueous solution) obtained by reaction with proportion described in Comparative Example 1 | — | 30 |
|   | Sodium lauroamphoacetate (30% aqueous solution) | 10 | 10 |
|   | Glycerol | 10 | 10 |
|   | Citric acid | Adjusted to pH 5.0 | Adjusted to pH 5.0 |
|   | Water | Residual | Residual |
|   | Total | 100 | 100 |
| Results | Foam quality | a | c |
|   | Bingham yield stress (Pa) | 10.3 | 7.0 |
|   | Sensory evaluation (Foam elasticity) | a | c |
|   | Sensory evaluation (Moisture retention after rinsing) | a | b |

The results described in Tables 1 and 2 show that the detergent compositions according to the present invention are excellent in storage stability due to suppressed precipitation, are satisfactory in lathering performance and foam quality that are indicated by the thickness and elasticity of a foam of the composition, and are excellent in moisture retention after rinsing. Thus, the detergent compositions of the present invention were demonstrated to be suited for use as cosmetics.

The invention claimed is:
1. A detergent composition, comprising:
(A) at least one N-unsaturated acyl acidic amino acid wherein the unsaturated acyl is a linear acyl having 8 to 20 carbon atoms;
(B) at least one N-saturated acyl acidic amino acid wherein the saturated acyl is a linear acyl having 8 to 14 carbon atoms; and
(C) optionally, at least one N-saturated acyl acidic amino acid wherein the saturated acyl is a linear acyl having 16 to 20 carbon atoms,
wherein
the weight ratio of said (A) to said (B) (A/B) is 0.01 to 0.80,
the weight ratio of said (C) to said (B) (C/B) is 0.00 to 0.32, and
a content of said (B) relative to a total content of said (A), (B), and (C) is 60 wt % or more, wherein when (C) is present, a content of said (C) relative to the total content of said (A), (B), and (C) is not more than 16 wt %, wherein said at least one N-unsaturated acyl acidic amino acid of (A) is an N-unsaturated acyl glutamic acid, and wherein said (B) comprises a N-decanoyl glutamate, a N-lauroyl glutamate, and a N-myristoyl glutamate.

2. The detergent composition according to claim 1, wherein said (A) is an N-unsaturated acyl acidic amino acid wherein the unsaturated acyl is a linear acyl having 16 to 20 carbon atoms.

3. The detergent composition according to claim 2, wherein said (A) is an N-oleoyl acidic amino acid.

4. The detergent composition according to claim 1, wherein said (B) further comprises an N-capryloyl acidic amino acid.

5. The detergent composition according to claim 1, wherein said (C) comprises one or more members selected from the group consisting of an N-palmitoyl acidic amino acid, an N-stearoyl acidic amino acid, and mixtures thereof.

6. The detergent composition according to claim 1, wherein one of said at least one N-unsaturated acyl acidic amino acid is an N-unsaturated acyl glutamic acid, and one of said at least one N-saturated acyl acidic amino acid is an N-saturated acyl glutamic acid.

7. The detergent composition according to claim 1, wherein the weight ratio of said (A) to said (B) (A/B) is 0.02 to 0.60.

8. The detergent composition according to claim 1, wherein the weight ratio of said (C) to said (B) (C/B) is 0.01 to 0.30.

9. The detergent composition according to claim 1, which has a pH of 4.0 to 7.0.

10. The detergent composition according to claim 9, which has a pH of 4.5 to 7.0.

11. A cosmetic, comprising a detergent composition according to claim 1.

12. The cosmetic according to claim 11, which has a pH of 4.5 to 7.0.

13. A method of washing skin or hair, comprising applying a detergent composition according to claim 1 to skin or hair.

14. The method according to claim 13, further comprising lathering and rinsing.

15. A method of treating skin or hair, comprising applying a detergent composition according to claim 1 to skin or hair.

* * * * *